(12) United States Patent
Kobayashi

(10) Patent No.: US 12,343,188 B2
(45) Date of Patent: Jul. 1, 2025

(54) IMAGE PROCESSING APPARATUS, RADIATION IMAGING SYSTEM, IMAGE PROCESSING METHOD, AND NON-TRANSITORY COMPUTER-READABLE STORAGE MEDIUM

(71) Applicant: CANON KABUSHIKI KAISHA, Tokyo (JP)

(72) Inventor: Tsuyoshi Kobayashi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 637 days.

(21) Appl. No.: 17/675,097

(22) Filed: Feb. 18, 2022

(65) Prior Publication Data

US 2022/0175331 A1  Jun. 9, 2022

Related U.S. Application Data

(63) Continuation of application No. PCT/JP2020/030949, filed on Aug. 17, 2020.

(30) Foreign Application Priority Data

Aug. 30, 2019  (JP) .................. 2019-158928

(51) Int. Cl.
*A61B 6/46* (2024.01)
*A61B 6/00* (2024.01)
(Continued)

(52) U.S. Cl.
CPC ............. *A61B 6/469* (2013.01); *A61B 6/468* (2013.01); *A61B 6/5205* (2013.01); *G06N 3/08* (2013.01); *G06T 3/4007* (2013.01); *G06T 3/4053* (2013.01)

(58) Field of Classification Search
CPC ....... A61B 6/469; A61B 6/468; A61B 6/5205; G06N 3/08; G06N 3/045; G06T 3/4007; G06T 3/4053
See application file for complete search history.

(56) References Cited

U.S. PATENT DOCUMENTS 9,418,417 B2   8/2016  Kobayashi
9,813,647 B2  11/2017  Kobayashi
(Continued)

FOREIGN PATENT DOCUMENTS

JP   H04-261649 A   9/1992
JP   2009-219140 A  9/2009
(Continued)

OTHER PUBLICATIONS

International Search Report issued by the Japan Patent Office on Nov. 2, 2020 in corresponding International Application No. PCT/JP2020/030949, with English translation.

(Continued)

*Primary Examiner* — Pinalben Patel
(74) *Attorney, Agent, or Firm* — Carter, DeLuca & Farrell LLP

(57) ABSTRACT

An image processing apparatus comprising a region extraction unit configured to perform region extraction processing of extracting a region from an input image acquired based on a radiographed image, wherein the region extraction unit comprises: a reduction unit configured to perform reduction processing for the input image to generate a reduced image; an inference unit configured to perform inference processing of, using the reduced image as an input, outputting an inferred image obtained by inferring the region in the reduced image; an enlargement unit configured to perform enlargement processing for the inferred image to generate an enlarged image; and a post-processing unit configured to (Continued)

perform post-processing of extracting the region from the enlarged image based on a feature of a shape of the region.

20 Claims, 5 Drawing Sheets

(51) Int. Cl.
   *G06N 3/08* (2023.01)
   *G06T 3/4007* (2024.01)
   *G06T 3/4053* (2024.01)

(56) References Cited

U.S. PATENT DOCUMENTS

| | | | |
|---|---|---|---|
| 9,979,911 B2 | 5/2018 | Kobayashi | |
| 11,625,561 B2 * | 4/2023 | Kuwajima | G06F 18/2431 382/159 |
| 2015/0080728 A1 * | 3/2015 | Uno | G06T 3/4092 345/428 |
| 2016/0239944 A1 * | 8/2016 | Bedi | G06V 10/462 |
| 2018/0000441 A1 * | 1/2018 | Wang | G06V 10/755 |
| 2020/0057907 A1 | 2/2020 | Kobayashi | |
| 2022/0036561 A1 * | 2/2022 | Liu | G06T 5/70 |
| 2022/0058423 A1 | 2/2022 | Kobayashi | |

FOREIGN PATENT DOCUMENTS

| | | |
|---|---|---|
| JP | 2018-114140 A | 7/2018 |
| JP | 2020-036773 A | 3/2020 |

OTHER PUBLICATIONS

Zhao, Liang, "Automatic Collimation Detection in Digital Radiographs with the Directed Hough Transform and Learning" International Workshop on Patch-based Techniques in Medical Imaging (Jan. 2016), pp. 71-78, vol. 9467 Chap.9, Nr.:558.

Notice of Reasons for Refusal issued by the Japanese Patent Office on Jul. 21, 2023 in corresponding JP Patent Application No. 2019-158928, with English translation.

* cited by examiner

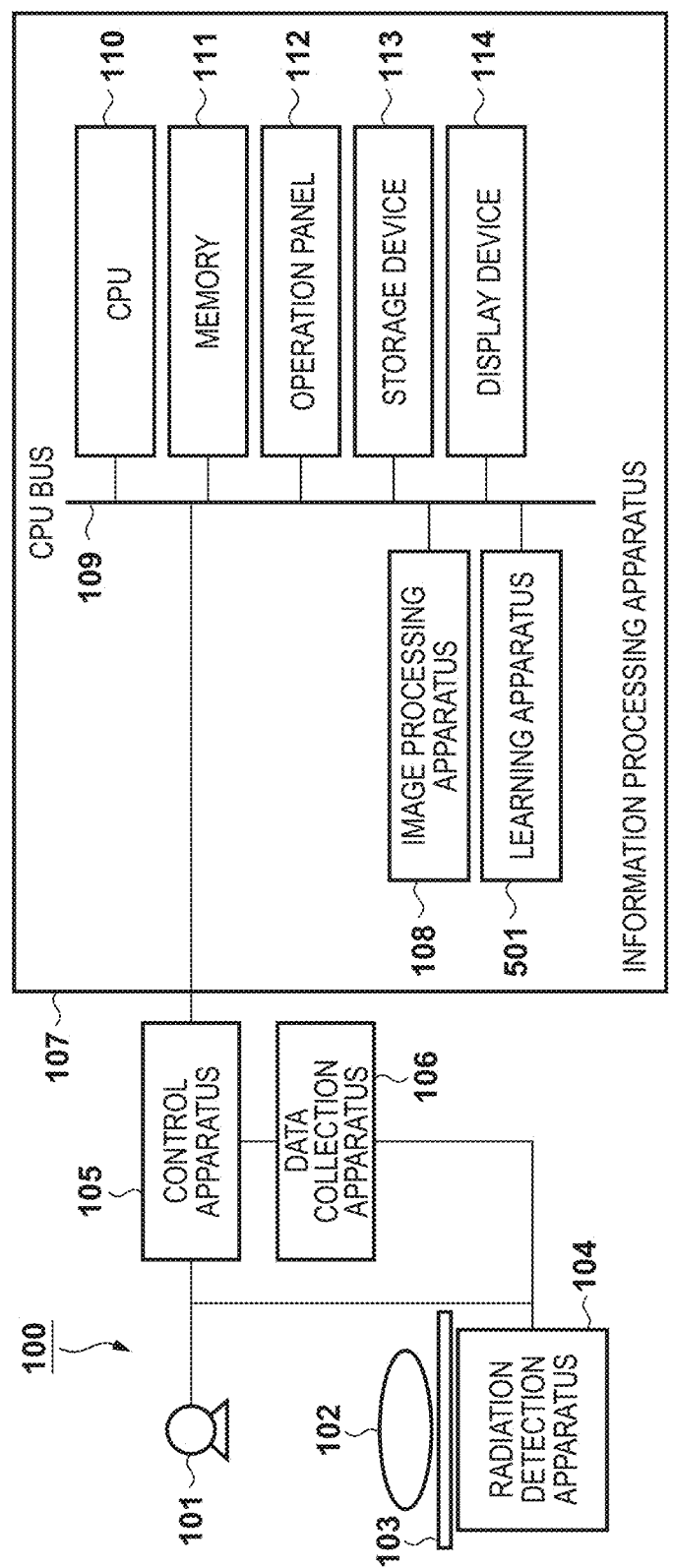

IMAGE PROCESSING APPARATUS, RADIATION IMAGING SYSTEM, IMAGE PROCESSING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2020/030949, filed Aug. 17, 2020, which claims the benefit of Japanese Patent Application No.2019-158928, filed Aug. 30, 2019, both of which are hereby incorporated by reference herein in their entirety.

BACKGROUND OF THE INVENTION

Field of the Invention

The present invention relates to an image processing apparatus, a radiation imaging system, an image processing method, and a program and, more particularly, to an image processing technique for performing region extraction processing of extracting a desired region in a radiographed image at a high speed and high accuracy.

Background Art

In recent years, radiation imaging apparatuses have widely proliferated in medical sites. A radiographic image is acquired as a digital signal, diagnostic image processing for converting it into an image suitable for a diagnosis is performed, and the image is displayed on a display device and used for a diagnosis.

In the diagnostic image processing of the radiation imaging apparatus, a desired region in the radiographic image is extracted, and the result of region extraction is used for processing. An example is extraction of a region (to be referred to as an "irradiation field" hereinafter) irradiated with radiation in the radiographic image. In the radiation imaging apparatus, generally, the irradiation field is limited using a diaphragm to reduce radiation exposure to parts other than a region of interest and prevent contrast from being lowered by scattered rays. To execute suitable diagnostic image processing for a diagnostic region of interest without any influence of the region where the radiation is shielded, it is necessary to use the result of correctly extracting the irradiation field in the image.

Concerning the technique for extracting a desired region, as exemplified by extraction of an irradiation field, various kinds of proposals have been made conventionally. For example, PTL 1 proposes a technique of inputting image data to a neural network, extracting an irradiation field, and outputting a result.

CITATION LIST

Patent Literature

PTL 1: Japanese Patent Laid-Open No. 04-261649

In the radiation imaging apparatus, to improve the throughput of a diagnosis, it is important to quickly display an image that has undergone suitable diagnostic image processing. Hence, region extraction processing needs to be accurately performed in a short time because its result is used in diagnostic image processing at the subsequent stage.

However, in the technique for extracting a region using a neural network, like PTL1, an enormous calculation amount poses a problem. In particular, convolutional neural networks (to be referred to as "CNNs" hereinafter), which have been applied in various fields in recent years due to their high accuracy, need a large calculation amount of a lot of convolutional operations, and long time needed for the processing can be one of the problems. If the resolution of an image to be input to a CNN is made low, the processing time is improved, but there may be a problem of accuracy. It is difficult to simultaneously implement a high processing speed and high accuracy.

The present invention has been made in consideration of the above-described problem, and provides an image processing technique capable of executing region extraction processing at a high speed and high accuracy.

SUMMARY OF THE INVENTION

According to one aspect of the present invention, there is provided an image processing apparatus comprising a region extraction unit configured to perform region extraction processing of extracting a region from an input image acquired based on a radiographed image, wherein the region extraction unit comprises: a reduction unit configured to perform reduction processing for the input image to generate a reduced image; an inference unit configured to perform inference processing of, using the reduced image as an input, outputting an inferred image obtained by inferring the region in the reduced image; an enlargement unit configured to perform enlargement processing for the inferred image to generate an enlarged image; and a post-processing unit configured to perform post-processing of extracting the region from the enlarged image based on a feature of a shape of the region.

According to another aspect of the present invention, there is provided an image processing method in an image processing apparatus comprising a region extraction unit configured to perform region extraction processing of extracting a region from an input image acquired based on a radiographed image, comprising: performing reduction processing for the input image to generate a reduced image; performing inference processing of, using the reduced image as an input, outputting an inferred image obtained by inferring the region in the reduced image; performing enlargement processing for the inferred image to generate an enlarged image; and performing post-processing of extracting the region from the enlarged image based on a feature of the region.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 5 is a block diagram showing an example of the basic configuration of a radiation imaging apparatus according to the second embodiment.

DESCRIPTION OF THE EMBODIMENTS

First Embodiment

Figure 1:
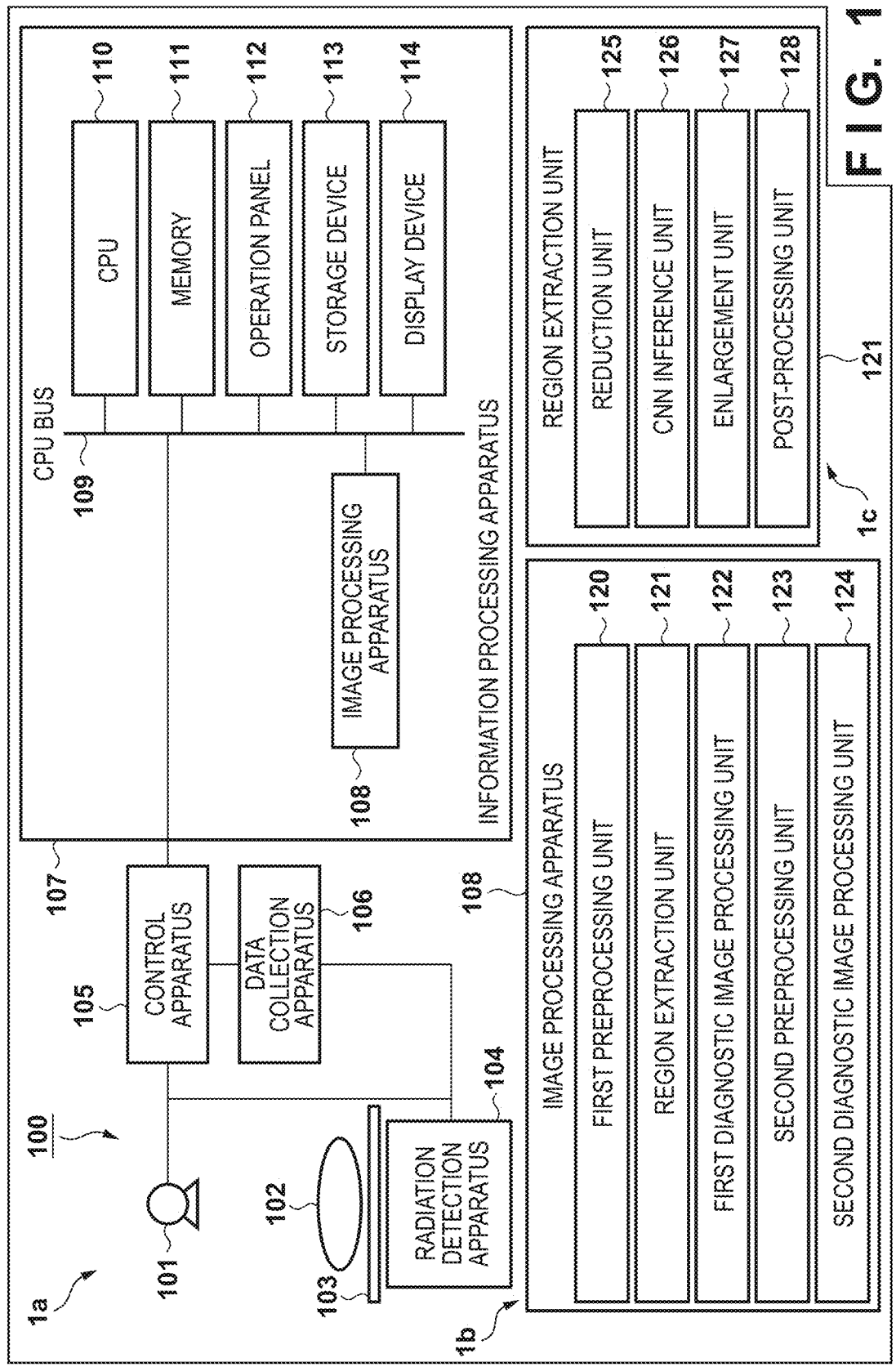
FIG. 1 shows a block diagram 1a showing an example of the basic configuration of a radiation imaging apparatus according to the first embodiment, a block diagram 1b showing an example of the basic configuration of an image processing apparatus, and a block diagram 1c showing an example of the basic configuration of a region extraction unit.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

An example of the configuration of a radiation imaging system according to the present invention will be described first with reference to FIG. 1. The radiation imaging system includes a radiation imaging apparatus and an image processing apparatus. In FIG. 1, 1a is a block diagram showing an example of the basic configuration of the radiation imaging apparatus according to the first embodiment. In FIG. 1, 1b is a block diagram showing an example of the basic configuration of the image processing apparatus. Also, 1c in FIG. 1 is a block diagram showing an example of the basic configuration of a region extraction unit.

A radiation imaging apparatus 100 includes a radiation generating apparatus 101 that generates radiation, a bed 103 on which an object 102 is arranged, a radiation detection apparatus 104 that detects the radiation and outputs image data according to the radiation that has passed through the object 102, a control apparatus 105 that controls the radiation generating timing and the radiation generating conditions of the radiation generating apparatus 101, a data collection apparatus 106 that collects various kinds of digital data, and an information processing apparatus 107 that controls image processing or the entire apparatus in accordance with a user instruction.

The information processing apparatus 107 includes an image processing apparatus 108, a CPU 110, a memory 111, an operation panel 112, a storage device 113, and a display device 114. These are electrically connected via a CPU bus 109.

The memory 111 stores various kinds of data necessary in processing of the CPU 110, and also includes a work memory for the CPU 110. The CPU 110 is configured to, using the memory 111, control the operation of the entire apparatus in accordance with a user instruction input to the operation panel 112.

In the first embodiment of the present invention, radiation is not limited to X-rays to be generally used and includes α-rays, β-rays, γ-rays, and the like, which are beams formed by particles (including photons) emitted upon radioactive decay, and beams (for example, particle rays and cosmic rays) with equal or higher energy.

In accordance with a user instruction via the operation panel 112, the radiation imaging apparatus 100 starts the imaging sequence of the object 102. The radiation generating apparatus 101 generates radiation under predetermined conditions, and the radiation detection apparatus 104 is irradiated with the radiation that has passed through the object 102. Here, the control apparatus 105 controls the radiation generating apparatus 101 based on radiation generating conditions such as a voltage, a current, and an irradiation time, and causes the radiation generating apparatus 101 to generate radiation under the predetermined conditions.

The radiation detection apparatus 104 detects the radiation that has passed through the object 102, converts the detected radiation into an electrical signal, and outputs image data according to the radiation. The image data output from the radiation detection apparatus 104 is collected as digital image data by the data collection apparatus 106. The data collection apparatus 106 transfers the image data collected from the radiation detection apparatus 104 to the information processing apparatus 107. In the information processing apparatus 107, the image data is transferred to the memory 111 via the CPU bus 109 under the control of the CPU 110.

The image processing apparatus 108 creates an image suitable for a diagnosis by applying various kinds of image processing to the image data stored in the memory 111, and stores the result in the storage device 113 or displays it on the display device 114.

As shown in 1b of FIG. 1, the image processing apparatus 108 includes, as functional components, a first preprocessing unit 120, a region extraction unit 121, a first diagnostic image processing unit 122, a second preprocessing unit 123, and a second diagnostic image processing unit 124. Also, as shown in 1c of FIG. 1, the region extraction unit 121 includes, functional components, a reduction unit 125, a CNN inference unit 126, an enlargement unit 127, and a post-processing unit 128.

Figure 2:
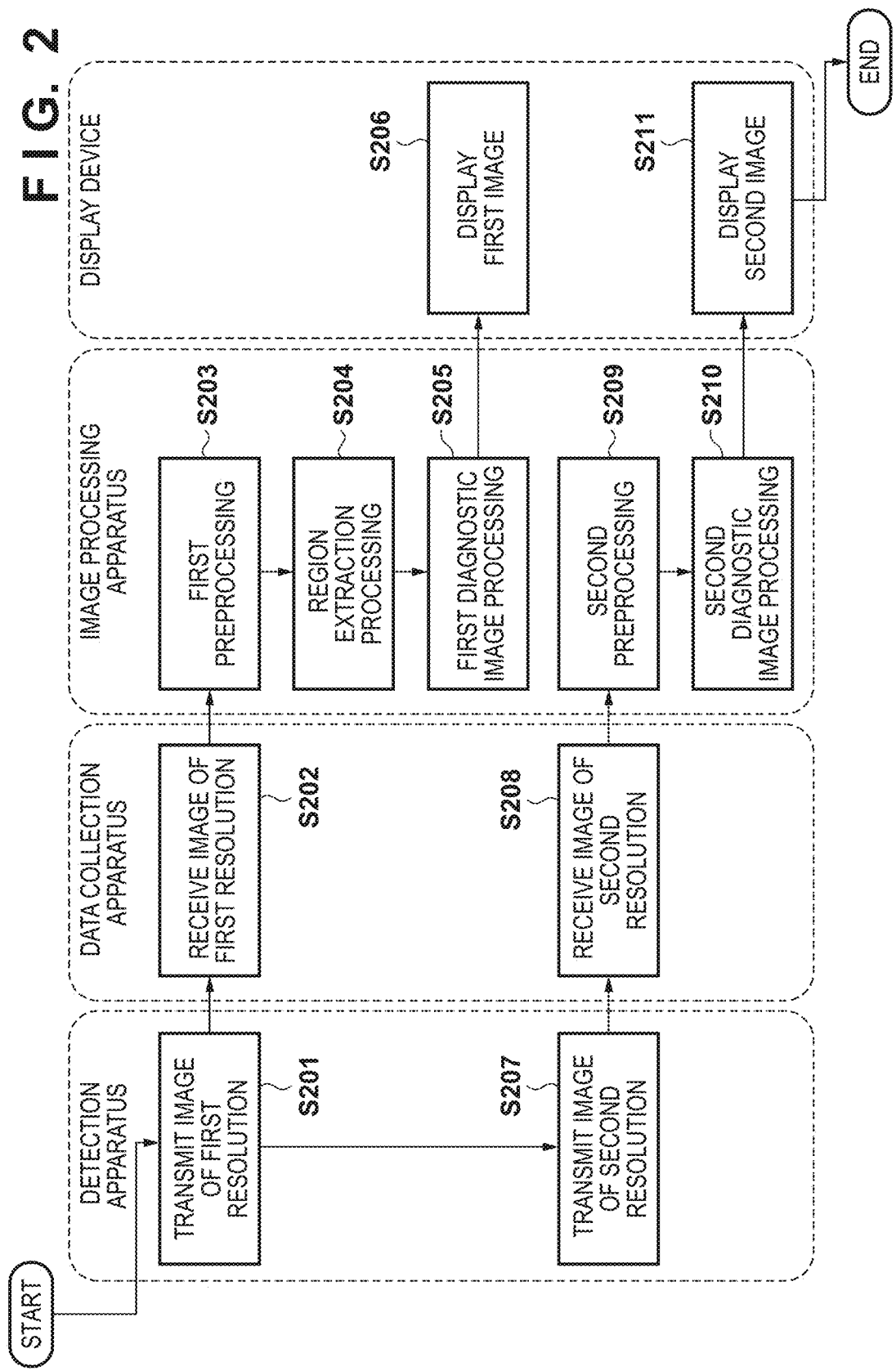
FIG. 2 is a flowchart showing the procedure of processing of the radiation imaging apparatus.

Processing of the radiation imaging apparatus 100 will be described next with reference to FIG. 2. FIG. 2 is a flowchart showing the procedure of processing of the radiation imaging apparatus 100.

In the radiation imaging apparatus 100, the radiation detection apparatus 104 can generate a high-resolution image formed from, for example, 2688 pixels×2688 pixels at maximum. In processing at the maximum resolution, however, since the image size is large, the transfer time to the data collection apparatus 106 and the processing time in the image processing apparatus 108 are long, and display on the display device 114 may take time.

To avoid the above-described phenomenon, speed up display on the display device 114, and improve the throughput of a diagnosis by the user, first, processing is performed at a first resolution lower than the maximum resolution in accordance with the processes of steps S201 to S206, and displays a first image. Then, processing is performed at a second resolution higher than the first resolution in accordance with the processes of steps S207 to S211, and displays a second image.

The CPU 110 controls display on the display device 114, and the display device 114 can display a first image to which first diagnostic image processing (first image processing) is applied, and a second image to which second diagnostic image processing (second image processing) is applied. When the first image is generated by the first diagnostic image processing unit 122, the display device 114 displays the first image. When the second image is generated by the second diagnostic image processing unit 124, the display device 114 switches the display of the first image and displays the second image. A detailed processing procedure will be described below.

In step S201, the radiation detection apparatus 104 generates an image of a first resolution and transmits it to the data collection apparatus 106. Here, the first resolution is lower than the maximum resolution (second resolution) of the radiation detection apparatus 104, and the radiation detection apparatus 104 generates an image by, for example, thinning the image width and the image height to ¼ or ⅛. As the method of thinning, for example, a method using only pixels arranged in an oblique direction in units of 4 pixels×4 pixels or 8 pixels×8 pixels or a method of averaging a plurality of pixels to do thinning can be used.

In step S202, the data collection apparatus 106 receives the digital data of the image of the first resolution transmitted from the radiation detection apparatus 104, and transfers it to the memory 111 of the information processing apparatus 107. Note that after the reception of the image of the first resolution by the data collection apparatus 106 is completed, processing of the radiation detection apparatus 104 advances to step S207, and the radiation detection apparatus 104 starts transmitting an image of a second resolution to the data collection apparatus 106. The process of step S207 is performed in parallel with the processes of steps S203 to S206, and time until display of the second image can be shortened.

In step S203, the first preprocessing unit 120 of the image processing apparatus 108 performs first preprocessing for the image of the first resolution transferred from the memory 111 of the information processing apparatus 107, and generates a first preprocessed image.

As the first preprocessing, the first preprocessing unit 120 can perform, for example, dark correction for correcting a dark current or fixed pattern noise of the radiation detection apparatus 104, gain correction for correcting the sensitivity between pixels of the radiation detection apparatus 104, defect correction for compensating for a defective pixel that outputs an abnormal value using pixels on the periphery in the radiation detection apparatus 104, grid stripe reduction for removing the stripes of a grid used in imaging, or logarithmic transformation processing of an image signal.

In step S204, the region extraction unit 121 performs region extraction processing for the first preprocessed image. The input image input to the region extraction unit 121 is the image (the image of the first resolution) acquired from the image captured using the radiation imaging apparatus 100, and the region extraction unit 121 extracts, as a desired region, the irradiation field irradiated with radiation by the radiation imaging apparatus 100. Using an arbitrary desired region as a target, the region extraction unit 121 can perform, as the region extraction processing, not only extraction of the irradiation field but also extraction of a specific organ of the object 102 or extraction of a direct line region where the radiation detection apparatus 104 is directly irradiated with radiation. Details of the region extraction processing will be described later.

In step S205, the first diagnostic image processing unit 122 performs first diagnostic image processing for the image that has undergone the region extraction processing, and generates a first diagnostic image. The first diagnostic image processing unit 122 performs the first diagnostic image processing (first image processing) for the image of the first resolution using the region extraction result (step S204) of the region extraction unit 121 using the image of the first resolution as the input image. The first diagnostic image processing unit 122 performs, as the first diagnostic image processing, for example, gradation processing, emphasis processing, noise reduction processing, scattered ray reduction processing, or the like, and generates an image suitable for a diagnosis. In the first diagnostic image processing, the result of region extraction obtained in step S204 can be used.

As an example of the region extraction result using method, the extraction result of the irradiation field is used for gradation processing. In this case, image analysis for performing appropriate gradation is performed while limiting the analysis range to the irradiation field, thereby implementing optimum gradation processing.

In addition, using the extraction result of a specific organ in the object 102, a desired organ may be specifically enhanced, or a desired organ may be displayed in an appropriate gradation. Alternatively, the extraction result of a direct line region may be used for scattered ray estimation in scattered ray reduction processing.

In step S206, the first image is displayed on the display device 114. The first image is the first diagnostic image obtained in step S205. When the first image is quickly displayed at a low resolution, the user can quickly grasp the image. The first image display can be done until second image display in step S211.

In step S207, the radiation detection apparatus 104 generates an image of a second resolution and transmits it to the data collection apparatus 106. Here, the second resolution is, for example, the maximum resolution of the radiation detection apparatus 104, and the radiation detection apparatus 104 transmits, to the data collection apparatus 106, the image of the resolution higher than the image of the first resolution transmitted in step S201.

In step S208, the data collection apparatus 106 receives the image of the second resolution transmitted from the radiation detection apparatus 104, and transfers it to the memory 111 of the information processing apparatus 107.

In step S209, the second preprocessing unit 123 of the image processing apparatus 108 performs second preprocessing for the image of the second resolution transferred from the memory 111 of the information processing apparatus 107, and generates a second preprocessed image.

In step S210, the second diagnostic image processing unit 124 performs second diagnostic image processing for the second preprocessed image, and generates a second diagnostic image. The second diagnostic image processing unit 124 performs the second diagnostic image processing (second image processing) for the image of the second resolution higher than the first resolution using the region extraction result (step S204) of the region extraction unit 121. The second diagnostic image processing unit 124 can perform, as the second diagnostic image processing, processing different from the first diagnostic image processing. However, if the first diagnostic image and the second diagnostic image are greatly different, the user may have a sense of discomfort. For this reason, it is preferable that gradation processing or emphasis processing that is almost the same as the first diagnostic image processing is applied as the second diagnostic image processing such that the first diagnostic image and the second diagnostic image have almost the same image quality except the resolution. The result of region extraction processing in step S204 can be used in the second diagnostic image processing after the resolution is converted.

In step S211, the second image is displayed on the display device 114. The second image is the second diagnostic image obtained in step S210. In this step, the first diagnostic image displayed on the display device 114 is switched to the second diagnostic image. Since the second diagnostic image is a high-resolution image as compared to the first diagnostic image, the user can grasp details of the image.

An example in which the second resolution is the maximum resolution of the radiation detection apparatus 104 has been described above. However, the present invention is not limited to this configuration, and, for example, the second resolution may be a resolution corresponding to the number of pixels that the display device 114 can display. This makes it possible to further shorten the processing time in steps S201 to S211 while ensuring a necessary and sufficient display resolution in the second image display. In this case, a third preprocessing unit and a third diagnostic image processing unit configured to process the image of the maximum resolution of the radiation detection apparatus 104 are further provided, and processing is performed in the same manner as steps S207 to S211.

Figure 3:
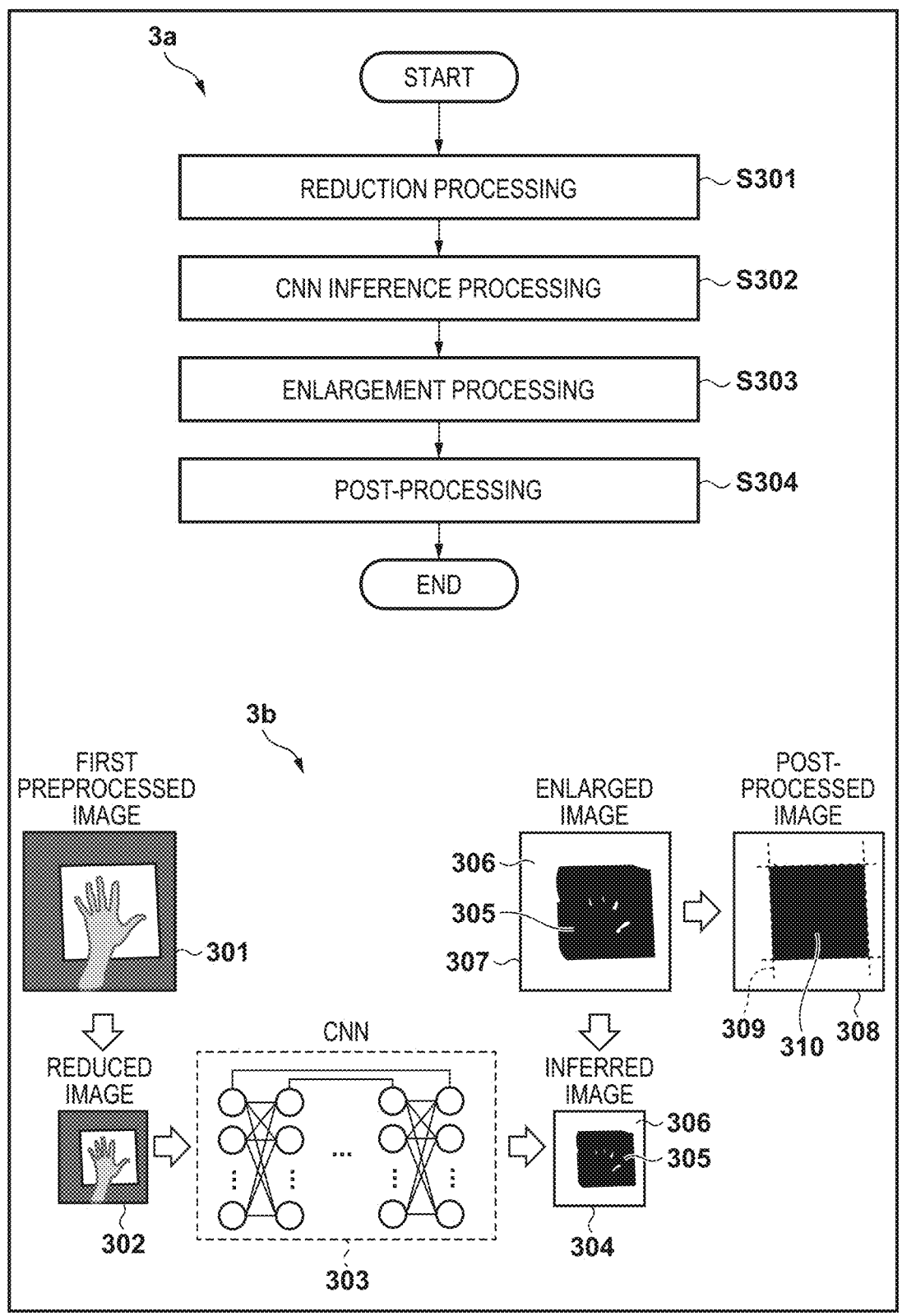
FIG. 3 shows a flowchart 3a showing the procedure of processing of the region extraction unit, and a view 3b schematically showing the concept of region extraction processing.

Detailed processing of region extraction processing by the region extraction unit 121 will be described next with reference to FIG. 3. In FIG. 3, 3a is a flowchart showing the procedure of processing of the region extraction unit 121. In FIG. 3, 3b is a view schematically showing the concept of region extraction processing. An example of processing of extracting an irradiation field in a radiographed image will be described below as region extraction processing.

In step S301, after a first preprocessed image 301 (input image) is input to the region extraction unit 121, the reduction unit 125 of the region extraction unit 121 performs reduction processing for the first preprocessed image 301 and generates a reduced image 302. The image size of the reduced image 302 is suitable for a convolutional neural network (CNN) 303 held by the CNN inference unit 126. An interpolation processing method used in image reduction is not limited. For example, a bilinear interpolation method, a bicubic interpolation method, a Lanczos interpolation method, or the like can be used, and the same interpolation processing method as that used to create the image used for the learning of the CNN 303 may be used.

In step S302, the CNN inference unit 126 performs inference processing (CNN inference processing) of, using the reduced image as an input, outputting an inferred image obtained by inferring a region in the reduced image. The CNN inference unit 126 is formed by the CNN 303 configured to, using the reduced image 302 as an input, output, as an inferred image 304, a labeling image generated by labeling the irradiation field of the extraction target by an arbitrary value. The CNN inference unit 126 performs the inference processing based on learning using a set of data including the reduced image 302 as an input and the labeling image as an output.

Here, as for the input/output of the CNN inference unit 126, the smaller the size of the reduced image 302 is, the higher the processing speed can be. Hence, the input size is preferably set equal to or smaller than the size of the first preprocessed image 301. However, when the size of the reduced image 302 is too small, the accuracy of region extraction processing tends to be lower. The inferred image 304 has a similar tendency. The simpler the output format is, the more the processing speed is improved. However, the accuracy tends to be lower.

From the above, the size of the reduced image 302 is preferably decided in consideration of the processing speed needed by the radiation imaging apparatus 100, accuracy needed in target region extraction, and the region extraction accuracy improving effect in steps S303 and S304 to be described later. In extraction of the irradiation field, for example, if the maximum resolution of the radiation detection apparatus 104 is 2688 pixels×2688 pixels, and the first resolution is ⅛ (336 pixels×336 pixels) the maximum resolution, the reduction unit 125 can set the image size of the reduced image 302 to about ¹/₁₆ (168 pixels×168 pixels) or ¹/₂₄ (112 pixels×112 pixels) the maximum resolution. In addition, the reduction unit 125 can also apply, to the reduced image 302, arbitrary normalization processing of, for example, setting the average to 0 and the variance to 1.

The image size of the inferred image 304 is preferably the same as the image size of the input image (reduced image 302) to the CNN 303. However, the CNN inference unit 126 can also set the image size of the inferred image 304 to ½ to ¼ the image size of the reduced image 302 in consideration of the processing speed needed by the radiation imaging apparatus 100, accuracy needed in target region extraction, and the region extraction accuracy improving effect in steps S303 and S304 to be described later. Here, the inferred image 304 output from the CNN 303 is a labeling image in which, for example, an irradiation field 305 of the extraction target is labeled to "1", and a region 306 other than that is labeled to "0". The CNN 303 can generate the labeling image by calculating the probability that each pixel of the inferred image 304 is an irradiation field as 0 to 1 and performing threshold processing using an arbitrary threshold of about 0.5.

Here, in the region extraction processing using the CNN 303, a case may occur in which the accuracy of the inferred image 304 is not sufficient, and it is not appropriate to directly use the inferred image 304 as the result of the region extraction unit 121 because it is difficult to increase the resolution of the image at the time of processing in the CNN 303 because of the problem of the processing speed, or because a partially wrong recognition result may be output if the reduced image 302 has a feature different from the learning data of the CNN 303.

For example, as a feature of an irradiation field, since a radiation diaphragm generally has a linear structure, the irradiation field is rectangular. However, a rectangular irradiation field is not always extracted in the inferred image 304 obtained by the CNN 303, and there may be a case in which the boundary is not linear or a case in which the irradiation field 305 slightly includes a detection error region. Hence, in following steps S303 and S304, processing of shaping the inferred image 304 based on the feature of the extraction target is performed.

In step S303, the enlargement unit 127 performs enlargement processing for the inferred image 304, and generates an enlarged image 307. This makes it possible to perform post-processing in step S304 at a high resolution and improve the accuracy of the final result. The enlargement unit 127 generates the enlarged image 307 such that it has a resolution higher than the resolution of the reduced image 302. The enlargement unit 127 can generate the enlarged image 307 to, for example, at least the same image size as the image size of the first preprocessed image 301 (the input image to the region extraction unit 121), and can also enlarge the enlarged image 307 to an image size equal to or larger than that of the first preprocessed image 301 depending on the type of post-processing in step S304. That is, the enlargement unit 127 can generate the enlarged image 307 to the same image size as the image size of the first preprocessed image 301 (the input image to the region extraction unit 121) or an image size larger than the image size of the input image.

As the enlargement processing, the enlargement unit 127 can perform pixel value interpolation processing, for example, a bilinear interpolation method, a bicubic interpolation method, or a Lanczos interpolation method. In addition, the enlargement unit 127 can also perform processing using a filter (for example, a two-dimensional filter) after the enlargement processing is performed. Alternatively, the enlargement unit 127 can perform enlargement processing using the information of a region in the first preprocessed image 301 at the time of enlargement processing. As the information of the first preprocessed image 301 to be used at the time of enlargement processing, the enlargement unit 127 can use, for example, a pixel value or edge intensity of a portion corresponding to the irradiation field 305.

In step S304, the post-processing unit 128 performs post-processing of extracting a region from the enlarged image 307 based on the feature of the shape of the region of the extraction target, and outputs a post-processed image 308.

In the example of irradiation field extraction, the post-processing unit 128 performs processing using the feature that the irradiation field has a rectangular shape. The post-processing unit 128 extracts a line corresponding to the boundary of the irradiation field of the input image from the enlarged image 307, thereby shaping the contour of the region. The post-processing unit 128 detects, from the enlarged image 307, the edge of the boundary formed by the irradiation field 305 and the region 306 other than that, and obtains a line 309 that forms the rectangular irradiation field. Details of processing of acquiring the line 309 will be described later. This can acquire an irradiation field 310 shaped into a rectangular shape.

The output in step S304 has a format of a labeling image in which, for example, the irradiation field like the post-processed image 308 is labeled to 1, and a region other than that is labeled to 0. However, the present invention is not limited to this, and, for example, a format of the vertex coordinates of the irradiation field 310 shaped into a rectangular shape or an equation representing the line 309 may be output.

By the above-described processes of steps S301 to S304, region extraction processing can be performed at a high speed and high accuracy.

As an example of detailed processing contents of the post-processing unit 128, processing contents of shaping the irradiation field to a rectangular shape when extracting the irradiation field will be described next with reference to FIG. 4. Note that the shape characteristic of the radiation diaphragm (the shape of the collimator) is not limited to a rectangular shape, and may be, for example, a circular shape or an elliptical shape.

Figure 4:
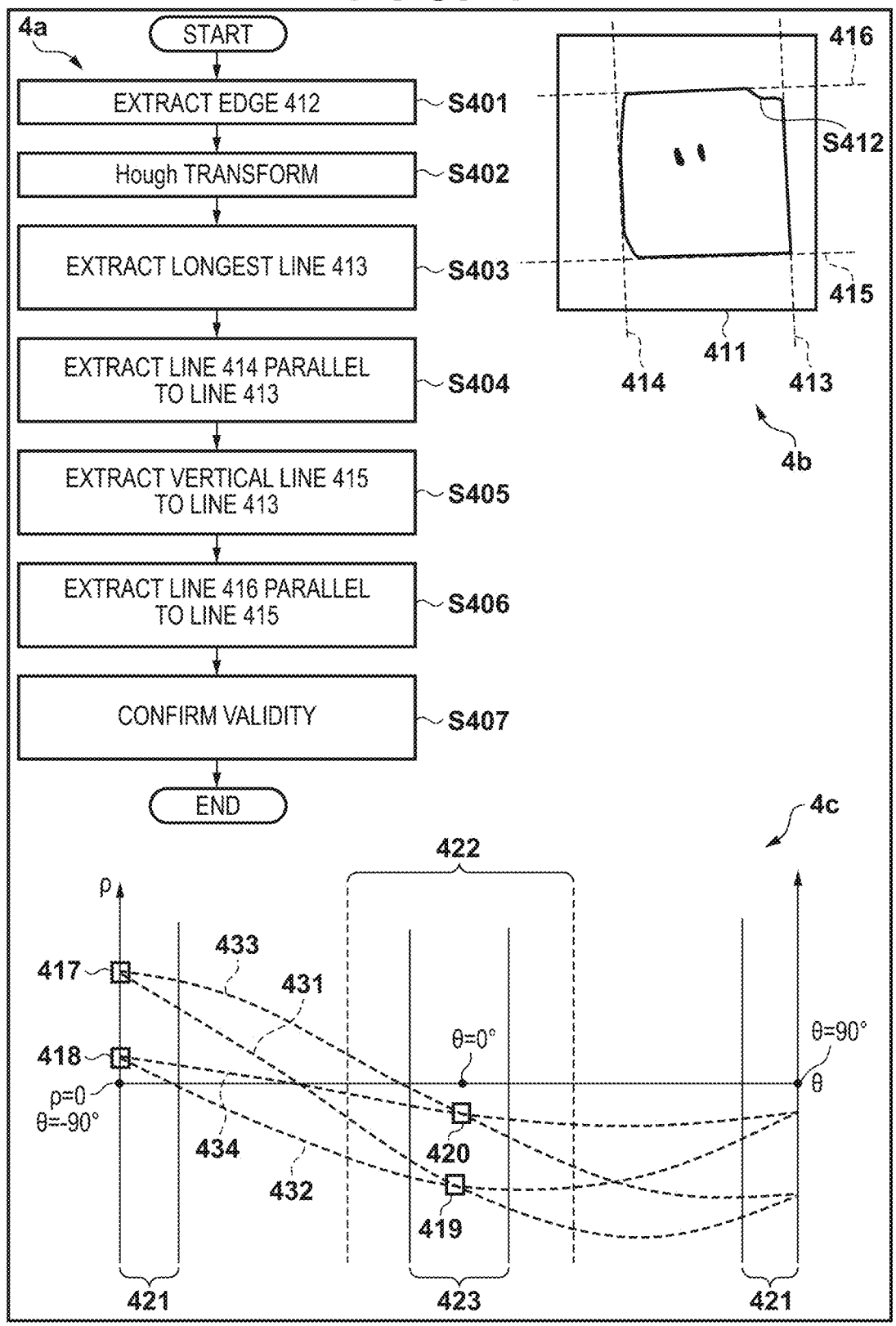
FIG. 4 shows a flowchart 4a showing the procedure of post-processing, a schematic view 4b showing an example of an intermediate image of post-processing, and a view 4c showing an example in which an image is converted into a polar coordinate space.

In FIG. 4, 4a is a flowchart showing the procedure of post-processing, 4b in FIG. 4 is a schematic view showing an example of an intermediate image of post-processing, and 4c in FIG. 4 is a view showing an example in which an image is converted into a polar coordinate space.

In step S401, the post-processing unit 128 extracts edge information from the enlarged image 307. The edge information extraction method is not limited. As an example, an edge can be extracted by applying a differential filter such as a sobel filter. By the above-described processing, an image 411 including an edge 412 including the contour of the irradiation field can be obtained.

In step S402, the post-processing unit 128 applies Hough transform to the image 411. Here, a point on the image 411, which is expressed as (x, y) on an orthogonal coordinate system, is converted into a polar coordinate system of an angle θ and a distance ρ using $$\rho = x \cos\theta + y \sin\theta$$

where θ is the angle made by the X-axis and a vertical line downward from the origin to a line passing through (x, y), and ρ is the length of the vertical line downward from the origin to the line passing through (x, y). For example, if transform is performed within the range of −90°<θ≤90°, a distribution on the polar coordinate system can be obtained, as shown in 4c of FIG. 4. Here, for the set of θ and ρ, which takes a local maximum value on the polar coordinate system, a line exists at high possibility in the image on the orthogonal coordinate system. When this feature is used, the effect of easily extracting the contour of the irradiation field having a linear structure by applying Hough transform can be obtained.

Note that if the image size of the enlarged image 307 is small, since it may be impossible to ensure a sufficient number of points on the image 411 expressed as (x, y) on the orthogonal coordinate system, and line extraction may not be appropriately performed, it is necessary to ensure a sufficient image size for the enlargement unit 127 to extract a line.

In step S403, the post-processing unit 128 extracts a longest line 413 from the image 411. In this step, the post-processing unit 128 searches the entire polar coordinate system and extracts a line formed by a set 417 of θ and ρ which take maximum values on the polar coordinate system.

In step S404, the post-processing unit 128 extracts a line 414 parallel to the line 413. Considering the shape characteristic of the radiation diaphragm (the shape of the collimator), it is considered that one more side exists in a direction parallel to one side of the rectangular shape of the irradiation field. Based on this assumption, on the polar coordinate system, a local maximum value is searched from a region 421 where θ exists within a predetermined range, using the set 417 of θ and ρ corresponding to the line 413 as a reference. As θ, for example, a value of about 5° to 15° with respect to θ=−90° or an arbitrary value of about −(5° to 15°) with respect to θ=90° can be set. This makes it possible to extract a set 418 of θ and ρ at the local maximum value and the line 414 corresponding to that.

In step S405, the post-processing unit 128 extracts a vertical line 415 as a line that crosses the line 413. Considering the shape characteristic of the radiation diaphragm (the shape of the collimator), it is considered that one more side exists in a direction vertical to one side of the rectangular shape of the irradiation field. Based on this assumption, on the polar coordinate system, the post-processing unit 128 searches for a set of θ and ρ which takes a local maximum value from a region 422 where θ exists within a predetermined range on the polar coordinate system, using the set 417 of θ and ρ corresponding to the line 413 as a reference. As the search range, arbitrary values within the range of about ±15° from θ=0° having a phase difference of +90° with respect to θ (=−90°) of the set 417 serving as a reference can be set. This allows the post-processing unit 128 to extract a set 419 of θ and ρ as a point where a waveform 431 passing through the set 417 of θ and ρ crosses a waveform 432 passing through the set 418 of θ and ρ, and the line 415 corresponding to that.

In step S406, the post-processing unit 128 extracts a line 416 parallel to the line 415. As in step S404, the post-processing unit 128 searches for a side in a direction parallel to the line 415 and extracts a set 420 of θ and ρ which takes a local maximum value from a region 423 on the polar coordinate system and the line 416 corresponding to that.

As the search range, the region 423 can be set in a narrow range, as compared to a region 422 where the set 419 of θ and ρ is extracted. The post-processing unit 128 extracts the set 420 of θ and ρ, in which a waveform 433 passing through the set 417 of θ and ρ crosses a waveform 434 passing through the set 418 of θ and ρ, and the line 416 corresponding to that from the region 423. Note that if no line is found in steps S403 to S406, the process of each step can be skipped while assuming that there exists no line.

In step S407, the post-processing unit 128 confirms validity concerning whether the lines 413 to 416 extracted in steps S403 to S406 are valid as the contour of the irradiation field. For example, the post-processing unit 128 can determine whether the length of an extracted line is longer than a predetermined value. Based on a line having a length more than a predetermined length in the lines extracted as contour candidates, the post-processing unit 128 shapes the contour of the irradiation field. Also, concerning the validity confirmation, the post-processing unit 128 can perform discrimination processing according to the feature of the captured image such as the imaging part of the object in radiation imaging.

The post-processing unit 128 excludes a line whose validity is not confirmed in this step, performs re-search as needed, and outputs a remaining line group as a final contour. By the above-described processes of steps S401 to S407, the post-processing unit 128 can appropriately shape the irradiation field and increase the accuracy of candidate region extraction.

As described above, according to the first embodiment, it is possible to provide an image processing technique capable of executing region extraction processing at a high speed and high accuracy.

Second Embodiment

A radiation imaging apparatus according to the second embodiment will be described next with reference to FIG. 5. FIG. 5 is a block diagram showing an example of the basic configuration of a radiation imaging apparatus 100 according to the second embodiment. The configuration according to the second embodiment is the same as in the first embodiment except that a learning apparatus 501 is included in an information processing apparatus 107.

In the first embodiment, the radiation imaging apparatus 100 is configured to perform CNN inference processing by the CNN inference unit 126 and perform learning of the convolutional neural network (CNN) 303 in advance. In the second embodiment, the radiation imaging apparatus 100 is configured to accumulate, in a storage device 113, a set of an image acquired in the use environment of a user and a set of data representing a desired extraction region such as a labeling image of an irradiation field. When the learning apparatus 501 is electrically connected to a CPU bus 109 in the information processing apparatus 107, the learning apparatus 501 can execute additional learning in the information processing apparatus 107 of the radiation imaging apparatus 100. The learning apparatus 501 performs learning of a CNN inference unit 126 using, as training data, a set of an image acquired in the use environment of the user and data representing a desired extraction region.

For learning of a convolutional neural network (CNN) 303, for example, it is preferable that learning is performed before introduction to the use environment of the user, and the parameter group of the learned CNN 303 is obtained in advance. However, it is also possible to update the parameter group of the CNN 303 in accordance with a use situation after introduction to the use environment of the user. In this case, a set of an image (radiographed image) acquired in the use environment of the user and data (the data of a labeling image) representing a desired extraction region (irradiation field) is stored as training data in the storage device 113.

Using the set of the data stored in the storage device 113 as new training data, the learning apparatus 501 can update the parameter group of the learned CNN 303 of the CNN inference unit 126 based on additional learning using the training data.

The CNN inference unit 126 performs inference processing based on the result of newly added learning and the result of learning performed in advance using, as training data, the set of the image (radiographed image) acquired in the use environment of the user and the data (the data of a labeling image) representing the desired extraction region (irradiation field). Note that since the calculation cost of learning of the CNN 303 is high, a calculation unit having high parallel calculation performance, such as a GPU, can also be used as the configuration of the learning apparatus 501.

As for the timing of performing additional learning, the learning apparatus 501 can select the timing of executing additional learning from, for example, the timing when a predetermined number or more of sets of data that are new training data are accumulated in the storage device 113, the timing when a predetermined number or more of sets of data in which the region extraction results (irradiation field recognition results) are corrected by the user are accumulated, and the like. In addition, as the initial value of the parameter group of the CNN inference unit 126 when performing additional learning, the parameter group of the learned CNN 303 used before the additional learning may be set to perform transfer learning.

Here, the storage device 113 and the learning apparatus 501 need not always be mounted on the information processing apparatus 107, and the storage device 113 and the learning apparatus 501 may be provided on a cloud server connected via a network. In this case, sets of data obtained by a plurality of radiation imaging apparatuses 100 may be collected/stored on the cloud server, and the learning apparatus 501 may perform additional learning using the set of data collected/stored on the cloud server.

As described above, according to the second embodiment, in addition to the effect of the first embodiment, it is possible to provide an image processing technique capable of performing suitable region extraction processing in accordance with the use environment of the user and capable of further increasing the extraction accuracy of a desired region.

According to the present invention, it is possible to provide an image processing technique capable of executing region extraction processing at a high speed and high accuracy.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus configured to perform region extraction processing of extracting a region from an input image acquired based on a radiographed image, wherein the image processing apparatus comprises:
   at least one processor; and
   at least one memory having stored thereon instructions which, when executed by the at least one processor, cause the image processing apparatus at least to:
      perform reduction processing for the input image to generate a reduced image;
      perform inference processing of, using the reduced image as an input, outputting an inferred image obtained by inferring the region in the reduced image using Convolutional Neural Network (CNN);
      perform enlargement processing for the inferred image to generate an enlarged image; and
      perform post-processing of extracting the region from the enlarged image based on a feature of a shape of the region.

2. The image processing apparatus according to claim 1, wherein the inference processing is performed by a convolutional neural network configured to, using the reduced image as an input, output, as the inferred image, a labeling image generated by labeling the region of an extraction target by an arbitrary value.

3. The image processing apparatus according to claim 2, wherein the the inference processing is based on learning using a set of data including the reduced image as an input and the labeling image as an output.

4. The image processing apparatus according to claim 2, wherein the the inference processing is based on a result of newly added learning and a result of learning performed in advance using, as training data, a set of an image acquired in a use environment of a user and data of the labeling image.

5. The image processing apparatus according to claim 2, wherein the instructions, when executed by the at least one processor, further cause the image processing apparatus at least to:
   perform learning of the inference processing using, as training data, a set of the images acquired in a use environment of a user and data representing the region,
   wherein the learning updates a parameter of the convolutional neural network of the inference processing based on additional learning using the training data.

6. The image processing apparatus according to claim 1, wherein the enlargement processing generates the enlarged image such that the enlarged image has a resolution higher than a resolution of the reduced image.

7. The image processing apparatus according to claim 1, wherein the enlargement processing generates the enlarged image to an image size equal to an image size of the input image or an image size larger than the image size of the input image.

8. The image processing apparatus according to claim 1, wherein the enlargement processing is performed using information of the region in the input image.

9. The image processing apparatus according to claim 8, wherein the information of the region includes one of a pixel value and an edge intensity of a portion corresponding to the region.

10. The image processing apparatus according to claim 9, wherein the enlargement processing performs interpolation processing of the pixel value, and
   wherein the instructions, when executed by the at least one processor, further cause the image processing apparatus at least to: after the enlargement processing perform processing using a filter.

11. The image processing apparatus according to claim 1, wherein the instructions, when executed by the at least one processor, further cause the image processing apparatus at least to:
   using a region extraction result, of the region extraction processing using an image of a first resolution as the input image, perform first image processing for the image of the first resolution; and
   , using the region extraction result of the region extraction processing, perform second image processing for an image of a second resolution higher than the first resolution.

12. The image processing apparatus according to claim 11, wherein the instructions, when executed by the at least one processor, further cause the image processing apparatus at least to:
   display a first image to which the first image processing is applied and a second image to which the second image processing is applied,
   wherein the first image is displayed when the first image is generated by the first image processing , and
   switch the display of the first image and display the second image when the second image is generated by the second image processing.

13. The image processing apparatus according to claim 1, wherein
   the input image is an image acquired from an image captured using a radiation imaging apparatus, and
   the region extraction processing extracts, as the region, an irradiation field irradiated with radiation by the radiation imaging apparatus.

14. The image processing apparatus according to claim 1, wherein the post-processing shapes a contour of the region by extracting, from the enlarged image, a line corresponding to a boundary of an irradiation field of the input image.

15. The image processing apparatus according to claim 14, wherein the post-processing shapes the contour of the region based on a line having a length more than a predetermined length in lines extracted as contour candidates.

16. A radiation imaging system comprising:
an image processing apparatus according to claim 1; and
a radiation imaging apparatus configured to acquire a radiographed image.

17. An image processing method in an image processing apparatus-configured to perform region extraction processing of extracting a region from an input image acquired based on a radiographed image, comprising:
performing reduction processing for the input image to generate a reduced image;
performing inference processing of, using the reduced image as an input, outputting an inferred image obtained by inferring the region in the reduced image using Convolutional Neural Network (CNN);
performing enlargement processing for the inferred image to generate an enlarged image; and
performing post-processing of extracting the region from the enlarged image based on a feature of the region.

18. The image processing method according to claim 17, further comprising:
performing first image processing for an image of a first resolution, using a region extraction result, of the region extraction processing using the image of the first resolution as the input image; and
performing second image processing for an image of a second resolution higher than the first resolution, using the region extraction result of the region extraction processing.

19. The image processing method according to claim 18, further comprising controlling a display configured to display a first image to which the first image processing is applied and a second image to which the second image processing is applied,
wherein in the controlling,
when the first image is generated in performing the first image processing, the display is caused to display the first image, and
when the second image is generated in performing the second image processing, the display of the first image is switched, and the display is caused to display the second image.

20. A non-transitory computer-readable storage medium storing a program for causing a computer to execute the image processing method according to claim 17.

* * * * *